United States Patent [19]

Behrens et al.

[11] Patent Number: 5,064,883

[45] Date of Patent: Nov. 12, 1991

[54] STABILIZATION OF ACID CATALYZED THERMOSET RESINS WITH N-HYDROXY HINDERED AMINES

[75] Inventors: Rudolf A. Behrens, New Fairfield, Conn.; Roger F. Malherbe, Basel, Switzerland

[73] Assignee: Ciba-Geigy Corporation, Ardsley, N.Y.

[21] Appl. No.: 259,944

[22] Filed: Oct. 19, 1988

Related U.S. Application Data

[63] Continuation-in-part of Ser. No. 99,413, Sep. 21, 1987, abandoned.

[51] Int. Cl.[5] .......... C08K 5/3492

[52] U.S. Cl. .......... 524/95; 524/91; 524/99; 524/100; 524/101; 524/102; 524/103; 524/133; 524/147; 524/191; 524/359

[58] Field of Search .......... 524/95, 99, 100, 101, 524/102, 103; 544/198, 351, 383, 384; 546/19, 20, 186, 188, 189, 245

[56] References Cited

U.S. PATENT DOCUMENTS

| | | | |
|---|---|---|---|
| 4,315,848 | 2/1982 | Dexter et al. | 525/124 |
| 4,402,983 | 9/1983 | Craven | 524/99 |
| 4,423,685 | 11/1986 | Minagawa et al. | 524/103 |
| 4,426,472 | 1/1984 | Berner | 524/99 |
| 4,472,547 | 9/1984 | Malherbe | 524/98 |
| 4,665,185 | 5/1987 | Winter | 546/184 |
| 4,668,721 | 5/1987 | Seltzer et al. | 524/95 |
| 4,691,015 | 9/1987 | Behrens et al. | 524/102 |
| 5,015,680 | 5/1991 | Finke et al. | 524/99 |

OTHER PUBLICATIONS

Journal of Polymer Science, Polymer Chemistry Ed., 22, 277-81 (1984).

*Primary Examiner*—Kriellion S. Morgan
*Attorney, Agent, or Firm*—Harry Falber

[57] ABSTRACT

N-hydroxy substituted hindered amine light stabilizers impart outstanding stabilization properties to acid catalyzed thermoset coating compositions with enhanced resistance against the deleterious effects of light, moisture or oxygen in the substantial absence of cure inhibition.

18 Claims, No Drawings

STABILIZATION OF ACID CATALYZED THERMOSET RESINS WITH N-HYDROXY HINDERED AMINES

BACKGROUND OF THE INVENTION

The instant invention pertains to the stabilization of acid catalyzed thermosetting resins as used in baked enamels or stoving lacquers by use of hindered amine light stabilizers substituted on the hindered N-atom by a hydroxyl group.

Hindered amine light stabilizers are well known to be effective in stabilizing a host of organic substrates including polymers from the deleterious effects of oxygen and light.

Such hindered amine light stabilizers have been used in stabilization of hot-crosslinkable alkyd or acrylic metallic stoving lacquers (U.S. Pat. No. 4,426,472) and in stabilizing acid-catalyzed stoving lacquers based on hot-crosslinkable acrylic polyester or alkyd resins (U.S. Pat. Nos. 4,344,876 and 4,426,471). None of the hindered amine light stabilizers of these patents possess structures having a hydroxyl group substituted directly on the N-atom of the hindered piperidine ring.

In their industrial uses, enamels with high solids content based on crosslinkable acrylic, polyester, urethane or alkyd resins are cured with an additional acid catalyst. Light stabilizers containing a basic nitrogen group are generally less than satisfactory in this application. Formation of a salt between the acid catalyst and the light stabilizer leads to incompatibility or insolubility and precipitation of the salt and to a reduced level of cure and to reduced light protective action and poor resistance to moisture.

THE INVENTION

The present invention relates to the use of N-hydroxy-2,2,6,6-tetralkylpiperidine or piperazine compounds, optionally together with further stabilizers for protecting acid-catalyzed thermosetting resins such as acrylic, polyester, polyurethane, polyamide or alkyd resins against the action of light, moisture, and oxygen.

The N-hydroxy compounds of the present invention are less basic than the corresponding hindered amine compounds from which they are derived, yet still exhibit undiminished, indeed enhanced, light stabilization efficacy.

The aforementioned problems encountered with use of compounds having a basic N-atom with acid catalyzed thermoset enamels were addressed in U.S. Pat. Nos. 4,344,876 and 4,426,471. Substitution of the N-atom of the hindered amines with an inert blocking group such as alkyl, alkenyl, benzyl, alkanoyl and the like clearly mitigated the difficulties and led to acid catalyzed thermoset enamels having acceptable light stabilization properties.

Substitution of the hindered N-atom of the hindered amines by hydroxyl as per the instant invention provides even better light stabilization effects for the acid catalyzed thermoset enamels.

The present invention is concerned with the stabilizing of acid catalyzed stoving lacquers based on hot crosslinkable acrylic, polyester, polyurethane, polyamide or alkyd resins against the action of light and moisture by the addition of N-hydroxyl substituted polyalkylpiperidine or other hindered amine derivatives, and with the stabilized acid catalyzed thermosetting resins thereby obtained.

On occasion, but especially in repairing finishes and lacquers with a high solids content (generally greater than 50% by weight) for use in industrial finishes, thermoset systems based on hot crosslinkable acrylic, modified acrylic, e.g. acrylic polyurethane, polyester, siliconized polyesters, polyester urethane or alkyd resins are provided with an additional acid catalyst. In such instances, however, failure symptoms caused by salt formation between light stabilizer and acid catalyst, delays in hardening, pigment flocculation and reduced light protective action are observed. These problems can be solved in a most satisfactory manner by means of the inventive use of N-hydroxyl substituted polyalkylpiperidine derivatives.

Accordingly, the present invention relates to the use of N-hydroxyl substituted 2,2,6,6-tetraalkylpiperidine or piperazine compounds optionally together with further stabilizers for stabilizing acid catalyzed baking finishes or coatings or thermoset coatings based on hot crosslinkable acrylic, modified acrylic, polyester, modified polyester or alkyd resins, in particular acrylic, polyester, polyurethane, polyamide or alkyd resins, against the action of light, moisture and oxygen.

The N-hydroxyl substituted hindered amine compounds of this invention contain a group of the formula

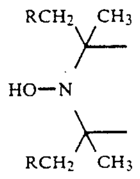

wherein R is hydrogen or methyl. Some are known compounds, e.g. U.S. Pat. No. 4,691,015, while others are claimed in copending application Ser. No. 99,418 now U.S. Pat. No. 4,831,139.

More particularly, the instant invention relates to the use in coatings of a hydroxylamine derivative having one of formulae A to O

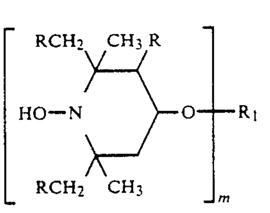

(A)

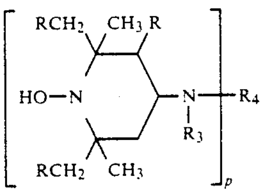

(B)

-continued (C)

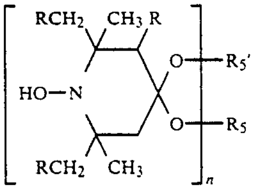

(D)

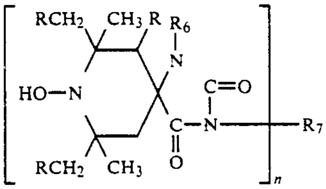

(E)

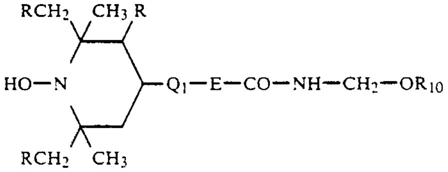

(F)

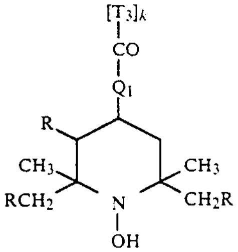

(G)

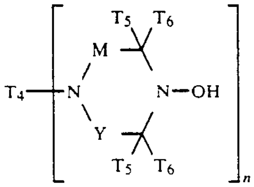

(H)

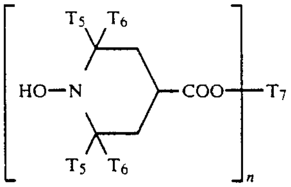

(I)

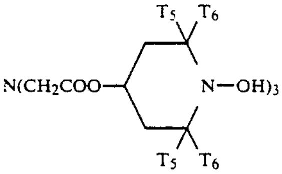

(J)

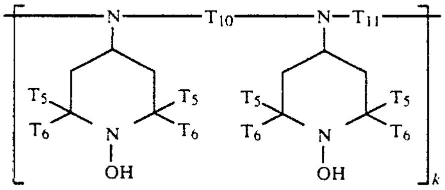

-continued (K)

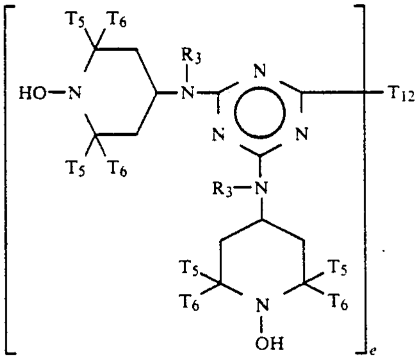

(L)

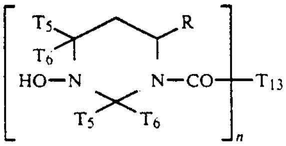

(M)

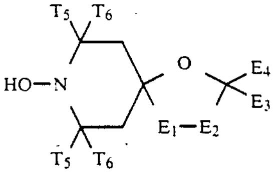

(N)

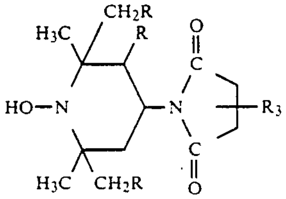

(O)

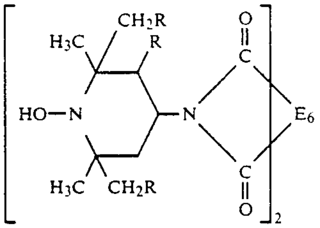

wherein

R is hydrogen or methyl, m is 1-4, when m is 1, $R_1$ is hydrogen, $C_1$-$C_{18}$ alkyl optionally interrupted by one or more oxygen atoms, $C_2$-$C_{12}$ alkenyl, $C_6$-$C_{10}$ aryl, $C_7$-$C_{12}$ aralkyl, glycidyl, a monovalent acyl radical or an aliphatic, cycloaliphatic, a araliphatic or aromatic carboxylic acid, or of a carbamic acid, preferably an acyl radical of an aliphatic carboxylic acid having 2-18 C atoms, of a cycloaliphatic carboxylic acid having 5-12 C atoms or of an aromatic carboxylic acid have 7-15 C atoms, or

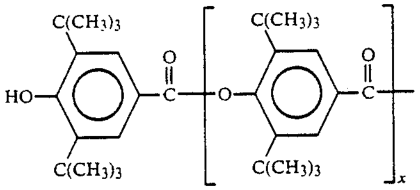

wherein x is 0 or 1, or

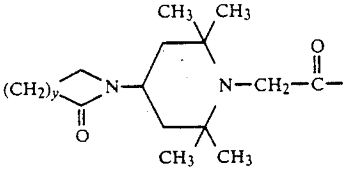

wherein y is 2–4;

when m is 2, $R_1$ is $C_1$–$C_{12}$ alkylene, $C_4$–$C_{12}$ alkenylene, xylylene, a divalent acyl radical of an aliphatic, cycloaliphatic, araliphatic or aromatic dicarboxylic acid or of a dicarbamic acid, preferably an acyl radical of an aliphatic dicarboxylic acid having 2–18 C atoms, of a cycloaliphatic or aromatic dicarboxylic acid having 8–14 C atoms, or of an aliphatic, cycloaliphatic or aromatic dicarbamic acid having 8–14 C atoms,

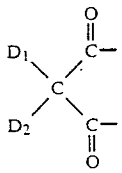

or

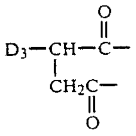

wherein $D_1$ and $D_2$ are independently hydrogen, an alkyl radical containing up to 8 carbon atoms, an aryl or aralkyl radical including 3,5-di-t-butyl-4-hydroxybenzyl radical, and $D_3$ is hydrogen, or an alkyl or alkenyl radical containing up to 18 carbon atoms;

when m is 3, $R_1$ is a trivalent acyl radical of an aliphatic, unsaturated aliphatic, cycloaliphatic, or aromatic tricarboxylic acid;

when m is 4, $R_1$ is a tetravalent acyl radical of a saturated or unsaturated aliphatic or aromatic tetracarboxylic acid including 1,2,3,4-butanetetracarboxylic acid, 1,2,3,4-but-2-enetetracarboxylic acid, and 1,2,3,5- and 1,2,4,5-pentanetetracarboxylic acid;

p is 1, 2 or 3, $R_3$ is hydrogen, $C_1$–$C_{12}$ alkyl, $C_5$–$C_7$ cycloalkyl, $C_7$–$C_9$ aralkyl, $C_2$–$C_{18}$ alkanoyl, $C_3$–$C_5$ alkenoyl or benzoyl;

when p is 1, $R_4$ is hydrogen, $C_1$–$C_{18}$ alkyl, $C_5$–$C_7$ cycloalkyl, $C_2$–$C_8$ alkenyl unsubstituted or substituted by a cyano, carbonyl or carbamide group, aryl, aralkyl, or it is glycidyl, a group of the formula $—CH_2—CH(OH)—Z$ or of the formula —CO—Z or —CONH—Z wherein Z is hydrogen, methyl or phenyl, or a group of the formulae

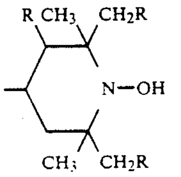

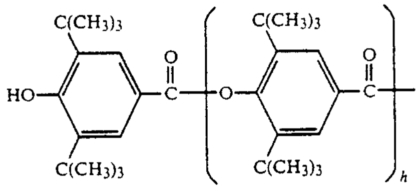

with h as 0 or 1;

or $R_3$ and $R_4$ together when p is 1 can be alkylene of 4 to 6 carbon atoms or 2-oxo-polyalkylene or the cyclic acyl radical of an aliphatic or aromatic 1,2- or 1,3-dicarboxylic acid, or when p is 2, $R_4$ is a direct bond or is $C_2$–$C_{12}$ alkylene, $C_6$–$C_{12}$ arylene, xylylene, a $—CH_2CH(OH)—CH_2$ group, or a group $—CH_2—CH(OH)—CH_2O—X—O—CH_2—CH(OH)—CH_2—$ wherein X is $C_2$–$C_{10}$ alkylene, $C_6$–$C_{15}$ arylene or $C_6$–$C_{12}$ cycloalkylene; or, provided that $R_3$ is not alkanoyl, alkenoyl or benzoyl, $R_4$ can also be a divalent acyl radical of an aliphatic, cycloaliphatic or aromatic dicarboxylic acid or dicarbamic acid, or can be the group —CO—;

$R_4$ is

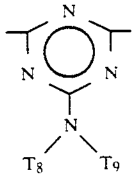

where $T_8$ and $T_9$ are independently hydrogen, alkyl of 1 to 18 carbon atoms, or $T_8$ and $T_9$ together are alkylene of 4 to 6 carbon atoms or 3-oxapentamethylene, preferably $T_8$ and $T_9$ together are 3-oxapentamethylene;

when p is 3, $R_4$ is 2,4,6-triazinyl, n is 1 or 2, when n is 1, $R_5$ and $R'_5$ are independently $C_1$–$C_{12}$ alkyl, $C_2$–$C_{12}$ alkenyl, $C_7$–$C_{12}$ aralkyl, or $R_5$ is also hydrogen, or $R_5$ and $R'_5$ together are $C_2$–$C_8$ alkylene or hydroxyalkylene or $C_4$–$C_{22}$ acyloxyalkylene;

when n is 2, $R_5$ and $R'_5$ together are $(—CH_2)_2C(CH_2—)_2$;

$R_6$ is hydrogen, $C_1$–$C_{12}$ alkyl, allyl, benzyl, glycidyl or $C_2$–$C_6$ alkoxyalkyl;

when n is 1, $R_7$ is hydrogen, $C_1$–$C_{12}$ alkyl, $C_3$–$C_5$ alkenyl, $C_7$–$C_9$ aralkyl, $C_5$–$C_7$ cycloalkyl, $C_2$–$C_4$ hydroxyalkyl, $C_2$–$C_6$ alkoxyalkyl, $C_6$–$C_{10}$ aryl, glycidyl, a group of the formula $—(CH_2)_t—COO—Q$ or of the formula $—(CH_2)_t—O—CO—Q$ wherein t is 1 or 2, and Q is $C_1$–$C_4$ alkyl or phenyl; or when n is 2, $R_7$ is $C_2$-$C_{12}$ alkylene, $C_6$-$C_{12}$ arylene, a group —$CH_2CH(OH)$—$CH_2$—O—X—O—$CH_2$—CH(OH)—$CH_2$— wherein X is $C_2$-$C_{10}$ alkylene, $C_6$-$C_{15}$ arylene or $C_6$-$C_{12}$ cycloalkylene, or a group —$CH_2CH(OZ')CH_2$—($OCH_2$—CH($OZ'$)$CH_2$)$_2$— wherein Z' is hydrogen, $C_1$-$C_{18}$ alkyl, allyl, benzyl, $C_2$-$C_{12}$ alkanoyl or benzoyl;

$Q_1$ is —N($R_8$)— or —O—; E is $C_1$-$C_3$ alkylene, the group —$CH_2$—CH($R_9$)—O— wherein $R_9$ is hydrogen, methyl or phenyl, the group —($CH_2$)$_3$—NH— or a direct bond;

$R_{10}$ is hydrogen or $C_1$-$C_{18}$ alkyl, $R_8$ is hydrogen, $C_1$-$C_{18}$ alkyl, $C_5$-$C_7$ cycloalkyl, $C_7$-$C_{12}$ aralkyl, cyanoethyl, $C_6$-$C_{10}$ aryl, the group —$CH_2$—CH($R_9$)—OH wherein $R_9$ has the meaning defined above; a group of the formula

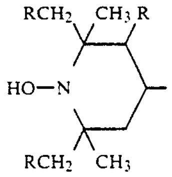

or a group of the formula

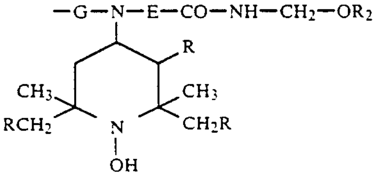

wherein G can be $C_2$-$C_6$ alkylene or $C_6$-$C_{12}$ arylene; or $R_8$ is a group —E—CO—NH—$CH_2$—$OR_{10}$;

Formula F denotes a recurring structural unit of a polymer where $T_3$ is ethylene or 1,2-propylene, or is the repeating structural unit derived from an alpha-olefin copolymer with an alkyl acrylate or methacrylate; preferably a copolymer of ethylene and ethyl acrylate, and where k is 2 to 100;

$T_4$ has the same meaning as $R_4$ when p is 1 or 2, $T_5$ methyl, $T_6$ is methyl or ethyl, or $T_5$ and $T_6$ together are tetramethylene or pentamethylene, preferably $T_5$ and $T_6$ are each methyl, M and Y are independently methylene or carbonyl preferably M is methylene and Y is carbonyl, and $T_4$ is ethylene where n is 2;

$T_7$ is the same as $R_7$, and $T_7$ is preferably octamethylene where n is 2, $T_{10}$ and $T_{11}$ are independently alkylene of 2 to 12 carbon atoms, or $T_{11}$ is

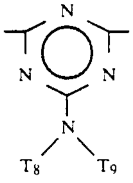

$T_{12}$ is piperazinyl,

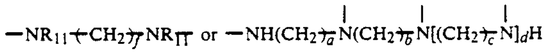

where $R_{11}$ is the same as $R_3$ or is also

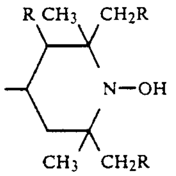

a, b and c are independently 2 or 3, and d is 0 or 1, preferably a and c are each 3, b is 2 and d is 1, and f is 0-20; and e is 2, 3 or 4, preferably 4;

$T_{13}$ is the same as $R_1$ with the proviso that $T_{13}$ cannot be hydrogen when n is 1;

$E_1$ and $E_2$, being different, each are —CO— or —N($E_5$)— where $E_5$ is hydrogen, $C_1$-$C_{12}$ alkyl or $C_4$-$C_{27}$ alkoxycarbonylalkyl, preferably $E_1$ is —CO— and $E_2$ is —N($E_5$)—;

$E_3$ is hydrogen, alkyl of 1 to 30 carbon atoms, phenyl, naphthyl, said phenyl or said naphthyl substituted by chlorine or by alkyl of 1 to 4 carbon atoms, or phenylalkyl of 7 to 12 carbon atoms, or said phenylalkyl substituted by alkyl of 1 to 4 carbon atoms, $E_4$ is hydrogen, alkyl of 1 to 30 carbon atoms, phenyl, naphthyl or phenylalkyl of 7 to 12 carbon atoms, or $E_3$ and $E_4$ together are polymethylene of 4 to 17 carbon atoms, or said polymethylene substituted by up to four alkyl groups of 1 to 4 carbon atoms, preferably methyl, and $E_6$ is an aliphatic or aromatic tetravalent radical.

Of particular interest are the hydroxylamine derivatives of formulae A, D, G-K or M.

In the structures A to O, if any substituents are $C_1$-$C_{18}$ alkyl, they are for example methyl, ethyl, n-propyl, n-butyl, sec-butyl, tert-butyl, n-hexyl, n-octyl, 2-ethylhexyl, n-nonyl, n-decyl, n-undecyl, n-dodecyl n-tridecyl, n-tetradecyl, n-hexadecyl or n-octadecyl. Typical cycloalkyl groups include cyclopentyl, cyclohexyl and cyclododecyl; typical cycloalkenyl groups include cyclohexenyl; while typical aralkyl groups include benzyl, alpha-methylbenzyl, alpha-dimethylbenzyl or phenethyl. $C_1$-$C_{12}$ alkyl and cyclohexyl are preferred.

If $R_1$ is a monovalent acyl radical of a carboxylic acid, it is for example an acyl radical of acetic acid, stearic acid, salicylic acid, benzoic acid or $\beta$-(3,5-di-tert-butyl-4-hydroxyphenyl) propionic acid.

If $R_1$ is a divalent acyl radical of a dicarboxylic acid, it is for example an acyl radical of oxalic acid, adipic acid, succinic acid, suberic acid, sebacic acid, phthalic acid, maleic acid, butyl-(3,5-di-tert-butyl-4-hydroxybenzyl)-malonic acid, or bicycloheptenedicarboxylic acid, with succinates, sebacates and phthalates being preferred.

If $R_1$ is a divalent acyl radical of a dicarbamic acid, it is for example an acyl radical of hexamethylenedicarbamic acid or of 2,4-toluylenedicarbamic acid.

The following compounds are examples of polyalkylpiperidine starting materials useful in making the hydroxylamine derivatives of formula A.

4-benzyloxy-2,2,6,6-tetramethylpiperidine 4-acryloyloxy-2,2,6,6-tetramethylpiperidine
4-hydroxy-2,2,6,6-tetramethylpiperidine
4-stearoyloxy-2,2,6,6-tetramethylpiperidine
di(2,2,6,6-tetramethylpiperidin-4-yl) adipate
di(2,2,6,6-tetramethylpiperidin-4-yl) sebacate,
di(2,2,6,6-tetramethylpiperidin-4-yl) phthalate
alpha,alpha'-(di-2,2,6,6-tetramethylpiperidine-4-oxy)-p-xylene
(2,2,6,6-tetramethylpiperidin-4-yl)-[4-(2-oxoazepin1-yl)-2,2,6,6-tetramethylpiperidin-4-yl]acetate.

If any substituents are $C_5$–$C_7$ cycloalkyl, they are in particular cyclohexyl.

As $C_7$–$C_9$ aralkyl, $R_3$ is particularly phenethyl or above all benzyl.

As $C_2$–$C_{18}$ alkanoyl, $R_3$ is for example propionyl, butyryl, octanoyl, dodecanoyl, hexadecanoyl, octadecanoyl, but preferably acetyl.

If $R_4$ is $C_2$–$C_8$ alkenyl unsubstituted or substituted by a cyano, carbonyl or carbamide group, it is for example 1-propenyl, allyl, methallyl, 2-butenyl, 2-pentenyl, 2-hexenyl, 2-octenyl, 2,2-dicyanovinyl, 1-methyl-2-cyano-2-methoxycarbonyl-vinyl or 2,2-diacetylaminovinyl.

If any substituents are $C_2$–$C_{12}$ alkylene, they are for example ethylene, propylene, 2,2-dimethylpropylene, tetramethylene, hexamethylene, octamethylene, decamethylene or dodecamethylene.

If any substituents are $C_6$–$C_{15}$ arylene, they are for example o-, m- or p-phenylene, 1,4-naphthylene or 4,4'-di-phenylene.

As $C_6$–$C_{12}$ cycloalkylene, X is especially cyclohexylene.

The following compounds are examples of polyalkylpiperidine starting materials useful in making the hydroxylamine derivatives of formula B.

N,N'-bis(2,2,6,6-tetramethylpiperidin-4-yl)-hexamethylene-1,6-diamine
N,N'-bis-(2,2,6,6-tetramethylpiperidin-4-yl)-hexamethylene-1,6-diacetamide
4-benzylamino-2,2,6,6-tetramethylpiperidine
N-n-butyl-N-(2,2,6,6-tetramethylpiperidin-4-yl)-4-hydroxy-3,5-di-tert.butyl benzamide
N,N'-bis-(2,2,6,6-tetramethylpiperidin-4-yl)-N,N'-dibutyl-adipamide
N,N'-bis-(2,2,6,6-tetramethylpiperidin-4-yl)-N,N'-dicyclohexyl-(2-hydroxypropylene-diamine)
N,N'-bis-(2,2,6,6-tetramethylpiperidin-4-yl)-p-xylylenediamine
4-(3-methyl-4-hydroxy-5-tert-butyl-benzoyl acetamido)-2,2,6,6-tetramethylpiperidine alpha-cyano-$\beta$-methyl-$\beta$-[N-(2,2,6,6-tetramethylpiperidin-4-yl]-amino-acrylic acid methyl ester If $R_5$ is $C_2$–$C_8$ alkylene or hydroxyalkylene, it is for example ethylene, 1-methyl-ethylene, propylene, 2-ethylpropylene or 2-ethyl-2-hydroxymethylpropylene.

As $C_4$–$C_{22}$ acyloxyalkylene, $R_5$ is for example 2-ethyl-2-acetoxymethyl-propylene.

The following compounds are examples for polyalkylpiperidine starting materials useful in making the hydroxylamine derivatives of formula C.

9-aza-8,8,10,10-tetramethyl-1,5-dioxaspiro[5.5]undecane,
9-aza-8,8,10,10-tetramethyl-3-ethyl-1,5-dioxaspiro-[5.5]undecane,
2,2,6,6-tetramethylpiperidine-4-spiro-2'-(1',3'-dioxane)-5'-spiro-5''-(1'',3''-dioxane)-2''-spiro-4'''-(2''',2'''-6''',6'''-tetramethylpiperidine).

If any substituents are $C_2$–$C_6$ alkoxyalkyl, they are for example methoxymethyl, ethoxymethyl, propoxymethyl, tert-butoxyethyl, ethoxyethyl, ethoxypropyl, n-butoxyethyl, tert-butoxyethyl, isopropoxyethyl or propoxypropyl.

If $R_7$ is $C_3$–$C_5$ alkenyl, it is for example 1-propenyl, allyl, methallyl, 2-butenyl or 2-pentenyl.

As $C_7$–$C_9$ aralkyl, $R_7$ is in particular phenethyl or above all benzyl; and as $C_5$–$C_7$ cycloalkyl, $R_7$ is especially cyclohexyl.

If $R_7$ is $C_2$–$C_4$ hydroxyalkyl, it is for example 2-hydroxyethyl, 2-hydroxypropyl, 3-hydroxypropyl, 2-hydroxybutyl or 4-hydroxybutyl.

As $C_6$–$C_{10}$ aryl, $R_7$ is in particular phenyl, or alpha- or $\beta$-naphthyl which is unsubstituted or substituted by halogen or $C_1$–$C_4$ alkyl.

If $R_7$ is $C_2$–$C_{12}$ alkylene, it is for example ethylene, propylene, 2,2-dimethylpropylene, tetramethylene, hexamethylene, octamethylene, decamethylene or dodecamethylene.

If $R_7$ is $C_6$–$C_{12}$ arylene, it is for example o-, m- or p-phenylene, 1,4-naphthylene or 4,4'-diphenylene.

If Z' is $C_2$–$C_{12}$ alkanoyl, it is for example propionyl, butyryl, octanoyl, dodecanoyl or preferably acetyl.

The following compounds are examples of polyalkylpiperidine starting materials useful in making hydroxylamine derivatives of formula D.

3-benzyl-1,3,8-triaza-7,7,9,9-tetramethylspiro[4.5]-decane-2,4-dione
3-n-octyl-1,3,8-triaza-7,7,9,9-tetramethylspiro[4.5]-decane-2,4-dione,
3-allyl-1,3,8-triaza-1,7,7,9,9-pentamethylspiro[4.5]-decane-2,4-dione or the compounds of the following formulae:

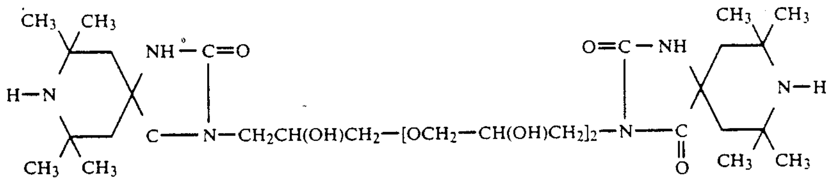

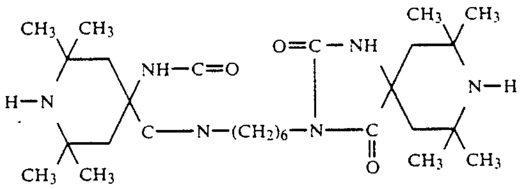

-continued

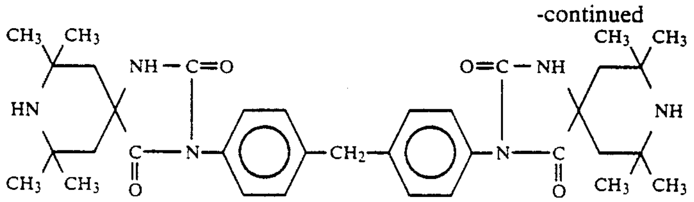

As $C_5$-$C_7$ cycloalkyl, $R_8$ is in particular cyclohexyl.

As $C_6$-$C_{10}$ aryl, $R_8$ is particularly phenyl, or alpha- or β-naphthyl which is unsubstituted or substituted with halogen or $C_1$-$C_4$ alkyl. As $C_1$-$C_3$ alkylene, E is for example methylene, ethylene or propylene.

As $C_2$-$C_6$ alkylene, G is for example ethylene, propylene, 2,2-dimethylpropylene, tetramethylene or hexamethylene; and as $C_6$-$C_{12}$ arylene, G is o-, m- or p-phenylene, 1,4-naphthylene or 4,4'-diphenylene.

The following compounds are examples of polyalkylpiperidine starting materials useful in making the hydroxylamine derivatives of formula E.

N-hydroxymethyl-N'-2,2,6,6-tetramethylpiperidin-4-ylurea

N-methoxymethyl-N'-2,2,6,6-tetramethylpiperidin-4-yl urea

N-methoxymethyl-N'-n-dodecyl-N'-2,2,6,6-tetramethylpiperidin-4-yl-urea, and

O-(2,2,6,6-tetramethylpiperidin-4-yl)-N-methoxymethylurethane.

When the instant hydroxylamine derivative is of formula F, the following polymeric compounds are examples of starting materials useful in preparing said derivatives.

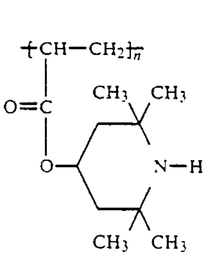

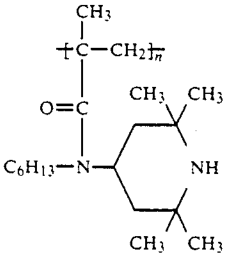

For compounds of formula N, $R_3$ is preferably $C_1$-$C_{12}$ alkyl and $C_5$-$C_7$ cycloalkyl and more preferably methyl, octyl, dodecyl and cyclohexyl.

For compounds of formula O, the following species are typical of tetracarboxylic acid dianhydrides suitable for the preparation thereof:

2,3,9,10-perylene tetracarboxylic acid dianhydride
1,4,5,8-naphthalene tetracarboxylic acid dianhydride
2,6-dichloronaphthalene-1,4,5,8-tetracarboxylic acid dianhydride
2,7-dichloronaphthalene-1,4,5,8-tetracarboxylic acid dianhydride
2,3,6,7-tetrachloronaphthalene-1,4,5,8-tetracarboxylic acid dianhydride
phenanthrene-1,8,9,10-tetracarboxylic acid dianhydride
2,3,3',4'-benzophenonetetracarboxylic acid dianhydride
pyromellitic dianhydride
3,3',4,4'-benzophenonetetracarboxylic acid dianhydride
2,2',3,3'-benzophenonetetracarboxylic acid dianhydride
3,3',4,4'-biphenyltetracarboxylic acid dianhydride
2,2',3,3'-biphenyltetracarboxylic acid dianhydride
4,4'-isopropylidenediphthalic anhydride
3,3'-isopropylidenediphthalic anhydride
4,4'-oxydiphthalic anhydride
4,4'-sulfonyldiphthalic anhydride
3,3'-oxydiphthalic anhydride
4,4'-methylenediphthalic anhydride
4,4'-thiodiphthalic anhydride
4,4'-ethylidenediphthalic anhydride
2,3,6,7-naphthalenetetracarboxylic acid dianhydride
1,2,4,5-naphthalenetetracarboxylic acid dianhydride
1,2,5,6-naphthalenetetracarboxylic acid dianhydride
benzene-1,2,3,4-tetracarboxylic acid dianhydride
pyrazine-2,3,5,6-tetracarboxylic acid dianhydride.

The following compounds are examples of hydroxylamines considered useful in the invention:

1. di-(1-hydroxy-2,2,6,6-tetramethylpiperidine-4-yl) methylmalonate
2. 1-hydroxy-4-salicyloxy-2,2,6,6-tetramethylpiperidine
3. di-(1-hydroxy-2,2,6,6-tetramethylpiperdine-4-yl) isophthalate
4. 1-hydroxy-2,2,6,6-tetramethylpiperidin-4-yl 3,5-di-tert-butyl-4-hydroxyhydrocinnamate
5. di(1-hydroxy-2,2,6,6-tetramethylpiperidin-4-yl) sebacate
6. di-(1-hydroxy-2,3,6-trimethyl-2,6-diethyl-piperidin-4-yl) phthalate
7. di-(1-hydroxy-2,2,6,6-tetramethylpiperidin-4-yl) n-butyl-(3,5-di-tert-butyl-4-hydroxybenzyl)malonate
8. hexane-1',6'-bis-(4-carbamoyloxy-1-hydroxy-2,2,6,6-tetramethylpiperidine)
9. N,N'-bis-(1-hydroxy-2,2,6,6-tetramethylpiperidin-4-yl)hexamethylene-1,6-diacetamide
10. 4-(N-cyclohexylacetamido)-1-hydroxy-2,2,6,6-tetramethylpiperidine
11. 1,6-di-(N-acetyl)-N-(1-hydroxy-2,2,6,6-tetramethylpiperidine-4-yl)]aminohexane
12. N-(1-hydroxy-2,2,6,6-tetramethylpiperidin-4-yl)epsilon-caprolactam
13. N-(1-hydroxy-2,2,6,6-tetramethylpiperidin-4-yl)succinimide
14. N-(1-hydroxy-2,3,6-trimethyl-2,6-diethyl-piperidin-4-yl)-maleimide
15. 8-aza-2,7,7,9,9-pentamethyl-8-hydroxy-1,4-dioxyspiro[4.5]decane
16. 9-aza-3-hydroxymethyl-3-ethyl-9-hydroxy-8,8,10,10-tetramethyl-1,5-dioxaspiro[5.5]undecane
17. 3-n-octyl-1,3,8-triaza-8-hydroxy-7,7,9,9-tetramethyl-spiro[4.5]decan-2,4-dione
18. 8-hydroxy-2,7,7,9,9-pentamethyl-2-hexyl-1-oxa-3,8-diazaspiro[4.5]decan-4-one
19. 3-hydroxy-2,2,4,4-tetramethyl-7-oxa-3,20-diazadispiro[5.1.11.2]heneicosan-21-one
20. 1,1'-ethylenebis-(4-hydroxy-3,3,5,5-tetramethylpiperazin-2-one)
21. 1,1'-sebacoyl-bis(3-hydroxy-2,2,4,4,6-pentamethylhexahydropyrimidine)
22. hydroxylamine derivative of polycondensation product of 2,4-dichloro-6-tert-octylamino-s-triazine and 4,4'-hexamethylenebis-(amino-2,2,6,6-tetramethylpiperidine)

23. N,N',N'',N'''-tetrakis[4,6-bis(butyl-(1-hydroxy-2,2,6,6-tetramethylpiperidin-4-yl)amino)-s-triazin-2-yl]1,10-diamino-4,7-diazadecane
24. hydroxylamine derivative of polycondensation product of 2,4-dichloro-6-morpholino-s-triazine and 4,4'-hexamethylenebis-(amino-2,2,6,6-tetramethylpiperidine)
25. 15-n-octadecyl-7-hydroxy-7,15-diazadispiro[5.1.5.3]-hexadecane-14,16-dione
26. 4-benzoyloxy-1-hydroxy-2,2,6,6-tetramethylpiperidine
27. 3-hydroxy-2,2,4,4-tetramethyl-20-(2-lauryloxycarbonyl)ethyl-7-oxa-3,20-diazadispiro[5.1.11.2]heneicosan-21-one
28. di-(1-hydroxy-2,2,6,6-tetramethylpiperidin-4-yl) phthalate
29. 1-hydroxy-2,2,6,6-tetramethylpiperidin-4-yl stearate
30. di-(1-hydroxy-2,2,6,6-tetramethylpiperidine-4-yl) terephthalate
31. 4-(4-tert.butylbenzoyloxy)-1-hydroxy-2,2,6,6-tetramethylpiperidine
32. (1-hydroxy-2,2,6,6-tetramethylpiperidin-4-yl)-4-hydroxy-3,5-di-tert.butylbenzoate
33. (1-hydroxy-2,2,6,6-tetramethylpiperidin-4-yl)-4-(4-hydroxy-3,5-di-tert.butylbenzoyloxy)-3,5-di-tert-.butylbenzoate
34. (1-hydroxy-2,2,6,6-tetramethylpiperidin-4-yl)-[4-(2-oxazepin-1-yl)-2,2,6,6-tetramethylpiperidin-4-yl) acetate
35. alpha,alpha'-di-(1-hydroxy-2,2,6,6-tetramethylpiperidin-4-oxy)-p-xylene
36. di-(1-hydroxy-2,2,6,6-tetramethylpiperidin-4-yl) diethylmalonate
37. N-n-butyl-N-(1-hydroxy-2,2,6,6-tetramethylpiperidin-4-yl)-4-hydroxy-3,5-di-tert.butylbenzamide
38. tetrakis (1-hydroxy-2,2,6,6-tetramethyl-4-piperidyl)-1,2,3,4-butane-tetracarboxylate
39. di-(1-hydroxy-2,2,6,6-tetramethylpiperidin-4-yl)isophthalate
40. di-(1-hydroxy-2,2,6,6-tetramethylpiperidin-4-yl)nbutylmalonate
41. di-(1-hydroxy-2,2,6,6-tetramethylpiperidin-4-yl)-2-(4-hydroxy 3,5-di-t.-butylbenzyl)-n-butylmalonate The hydroxylamine derivatives of the instant invention are generally prepared by oxidizing a hindered amine with an appropriate peroxy compound such as hydrogen peroxide or tert-butyl hydroperoxide in the presence of a metal carbonyl or metal oxide catalyst followed by reduction of the oxyl intermediate formed to the desired hydroxylamine derivative, preferably by catalytic hydrogenation.

The hindered amine precursors are largely commercially available or can be prepared by known methods.

The acrylic resin lacquers, which can be stabilized against light, moisture and oxygen in accordance with the invention, are the conventional acrylic resin stoving lacquers or thermosetting resins including acrylic/melamine systems which are described, for example, in H. Kittel's "Lehrbuch der Lacke und Beschichtungen", Vol. 1. Part 2, on pages 735 and 742 (Berlin 1972), "Lackkunstharze" (1977), by H. Wagner and H. F. Sarx, on pages 229–238, and in S. Paul's "Surface Coatings: Science and Technology" (1985).

The polyester lacquers, which can be stabilized against the action of light and moisture, are the conventional stoving lacquers described e.g. in H. Wagner and H. F. Sarx, op. cit., on pages 86–99.

The alkyd resin lacquers which can be stabilized against the action of light and moisture in accordance with the invention, are the conventional stoving lacquers which are used in particular for coating automobiles (automobile finishing lacquers), for example lacquers based on alkyd/melamine resins and alkyd/acrylic/melamine resins (see H. Wagner and H. F. Sarx, op. cit., pages 99–123). Other crosslinking agents include glycoluril resins, blocked isocyanates or epoxy resins.

The acid catalyzed stoving lacquers stabilized in accordance with the invention are suitable both for metal finish coatings and solid shade finishes, especially in the case of retouching finishes, as well as various coil coating applications. The lacquers stabilized in accordance with the invention are preferably applied in the conventional manner by two methods, either by the single-coat method or by the two-coat method. In the latter method, the pigment-containing base coat is applied first and then a covering coat of clear lacquer over it.

Although major emphasis in this application is directed to acid catalyzed baked finishes, it is also to be noted that the instant N-hydroxy substituted hindered amines are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, anhydrides, amines, and the like. Correspondingly, the epoxide may be utilized as the crosslinking agent for various acrylic or polyester resin systems that have been modified by the presence of reactive groups on the backbone structure.

The amount of polyalkylpiperidine derivative employed is 0.1 to 5% by weight, based on the solvent-free binder, preferably 0.5 to 2% by weight. The binders can be dissolved or dispersed in customary organic solvents or in water or can be solvent-free.

When used in two-coat finishes, the polyalkylpiperidine derivative can be incorporated in the clear coat or both in the clear coat and in the pigmented base coat.

To attain maximum light stability, the concurrent use of other conventional light stabilizers can be advantageous. Representative light stabilizers are UV absorbers of the benzophenone, benzotriazole, aryl substituted s-triazine, acrylic acid derivative, or oxalanilide type, or metal-containing light stabilizers, for example organic nickel compounds. In two-coat systems, these additional light stabilizers can be added to the clear coat and/or the pigmented base coat.

If such combinations are employed, the sum of all light stabilizers is 0.2 to 20% by weight, preferably 0.5 to 5% by weight, based on the film-forming resin.

Examples of the UV absorbers which may be used in the instant compositions in conjunction with the aforementioned piperidine compounds are:

(a) 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tertbutyl-, 4'-octoxy-, 3',5'-di-tert-amyl derivative.

(b) 2-Hydroxy-benzophenones, for example, the

If such combinations are employed, the sum of all light stabilizers is 0.2 to 20% by weight, preferably 0.5 to 5% by weight, based on the film-forming resin.

Examples of the UV absorbers which may be used in the instant compositions in conjunction with the aforementioned piperidine compounds are:

(a) 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tertbutyl-, 4'-octoxy-, 3',5'-di-tert-amyl derivative.

(b) 2-Hydroxy-benzophenones, for example, the 4-hydroxy-, 4-methoxy-, 4-octoxy-, 4-decyloxy-, 4-dodecyloxy-, 4-benzyloxy, 4,2',4'-trihydroxy- and 2'-hydroxy-4,4'-dimethoxy derivative.

(c) Acrylates, for example, alpha-cyano-$\beta$,$\beta$-diphenylacrylic acid ethyl ester or isoctyl ester, alphacarbomethoxy-cinnamic acid methyl ester, alpha-cyano-$\beta$-methyl-p-methoxy-cinnamaic acid methyl ester or butyl ester, alpha-carbomethoxy- p-methoxy-cinnamic acid methyl ester, N-($\beta$-carbomethoxy-$\beta$-cyanovinyl)-2-methyl-indoline.

(d) Nickel compounds, for example, nickel complexes of 2,2'-thiobis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl 4-hydroxy-, 4-methoxy-, 4-octoxy-, 4-decyloxy-, 4-ddecyloxy-, 4-benzyloxy, 4,2',4'-trihydroxy- and 2'-hydroxy-4,4'-dimethoxy derivative.

(c) Acrylates, for example, alpha-cyano-$\beta$,$\beta$-diphenylacrylic acid ethyl ester or isoctyl ester, alphacarbomethoxy-cinnamic acid methyl ester, alpha-cyano-$\beta$-methyl-p-methoxy-cinnamaic acid methyl ester or butyl ester, alpha-carbomethoxy- p-methoxy-cinnamic acid methyl ester, N-($\beta$-carbomethoxy-$\beta$-cyanovinyl)-2-methyl-indoline.

(d) Nickel compounds, for example, nickel complexes of 2,2'-thiobis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketonoxime, nickel complexes of 1-phenyl-4-lauroyl-5-hydroxy-pyrazol, optionally with additional ligands.

(e) Oxalic acid diamides, for example, 4,4'-di-octyloxyoxanilide, 2,2'-di-octyloxy-5,5'-di-tert-butyloxanilide, 2,2'-di-dodecyloxy-5,5'-di-tert-butyl-oxanilide, 2-ethoxy-2'-ethyl-oxanilide, N,N'-bis-(3-dimethylaminopropyl)-oxalamide, 2-ethoxy-5-tert-butyl-2'-ethyloxanilide and its mixture with 2-ethoxy-2'-ethyl-5,4'-ditert-butyloxanilide and its mixtures of ortho- and paramethoxy- as well as of o- and p-ethoxy-disubstituted oxanilides.

(f) Hydroxyphenyl s-triazines such as 2,6-bis(2,4-dimethylphenyl)-4-(2-hydroxy-4-octyloxyphenyl)-s-triazine or the corresponding 4-(2,4-dihydroxyphenyl) derivative.

Of particular value in the instant compositions are the benzotriazoles of high molecular weight and low volatility such as 2-[2-hydroxy-3,5-di(alpha,alpha-dimethylbenzyl)-phenyl]-2H-benzotriazole, 2-(2-hydroxy-3,5-di-tert-octylphenyl)-2H-benzotriazole, 2-(2-hydroxy-3-alpha,alpha-dimethylbenzyl-5-tert-octyl-phen yl)-2H-benzotriazole, 2-(2-hydroxy-3-tert-octyl-5, alpha,alpha-dimethylbenzylphenyl)-2H-benzotriazole, 2-(2-hydroxy-3,5-di-tert-amylphenyl)-2H-benzotriazole, dodecylated 2-[2-hydroxy-5-methylphenyl)-2H-benzotriazole, 2-[2-hydroxy-3-tert.butyl-5-(2-octyloxycarbonyl)ethylphenyl]-2H-benzotriazole and the 5-chloro compounds corresponding to each of the above named benzotriazoles.

Most preferably the benzotriazoles useful in the instant compositions are 2-[2-hydroxy-3,5-di(alpha,alpha-dimethyl-benzyl)phenyl]-2H-benzotriazole, dodecylated 2-[2-hydroxy-5-methylphenyl-2H-benzotriazole, 2-[2-hydroxy-3-tert-butyl-5-(2-(omega-hydroxy-octa-(ethyleneoxy)carbonyl)-ethylphenyl]-2H-benzotriazole, 2-[2-hydroxy-3-tert.butyl-5-(2-octyloxycarbonyl)ethylphenyl]-2H-benzotriazole and 5-chloro-2-[2-hydroxy-3-tert.butyl-5-(2-octyloxycarbonyl)ethylphenyl]-2H-benzotriazole.

A preferred embodiment of the instant invention pertains to stabilized compositions comprising (a) an acid catalyzed thermoset coating or enamel based on hot crosslinkable acrylic, polyester or alkyd resins, (b) an N-hydroxyl substituted 2,2,6,6-tetraalkylpiperidine compound, and a UV absorber selected from (c) the group consisting of the benzophenones, benzotriazoles, aryl substituted s-triazines, acrylic acid derivatives, organic nickel compounds and oxanilides.

Further optional ingredients are antioxidants, for example, those of the sterically hindered phenol derivatives, phosphorus compounds, such as phosphites, phosphines or phosphonites, plasticizers, levelling assistants, hardening catalysts, thickeners, dispersants or adhesion promoters.

A further preferred embodiment of the instant invention is a stabilized composition containing components (a), (b) and (c) described above which additionally contains as component (d) a phosphite or phosphonite.

The amount of phosphite or phosphonite (d) which is used in the instant compositions is from 0.05 to 2% by weight, preferably from 0.1 to 1% by weight, based on the film forming resin. In two-coat systems, these stabilizers may be added to the clear coat and/or the base coat.

Typical phosphite and phosphonites include triphenyl phosphite, diphenylalkyl phosphites, phenyldialkyl phosphitetri-(nonylphenyl)phosphite, trilauryl phosphite, trioctadecyphosphite, di-stearyl-pentaerythritol diphosphite, tris-(2,4-di-tert.butylphenyl) phosphite, di-isodecylpentaerythritol diphosphite, di-(2,4-di-tert.butylphenyl)pentaerythritol diphosphite, tristearylsorbitol triphosphite, tetrakis-(2,4 di-tert.butylphenyl)-4,4'-diphenylylenediphosphonite.

The acid catalyzed thermoset enamels must be stabilized in order to function acceptably in end-use applications. The stabilizers are needed to impart greater retention of durability to the cured enamels (as measured by 20° gloss, distinction of image, cracking or chalking); the stabilizers must not retard cure (normal bake for auto finishes at 121° C. and low bake repair at 82° C. (as measured by hardness, adhesion, solvent resistance and humidity resistance), the enamel should not yellow on curing and further color change exposure to light should be minimized; the stabilizers would be soluble in the organic solvents normally used in coating applications such as methyl amyl ketone, xylene, n-hexyl acetate, alcohol and the like.

The instant hindered amine light stabilizers substituted on the N-atom by a hydroxyl moiety fulfill each of these requirements and provide alone or in combination with a UV-absorber outstanding light stabilization protection to the cured acid catalyzed thermoset enamels.

The following examples describe the inventive use of N-hydroxyl substituted polyalkylpiperidine derivatives in acid catalyzed stoving lacquers based on acrylic resin containing binder systems. Parts and percentages are by weight.

EXAMPLE 1

Stabilization of High Solids Acid-catalyzed, Thermoset Acrylic Resin Enamel

A high solids (50% by weight) thermoset acrylic resin enamel, catalyzed by 0.5% by weight of p-toluenesulfonic acid, based on the film-forming resin, is stabilized by the addition of various N-hydroxy-polyalkylpiperidine derivatives.

The high solids thermoset acrylic resin enamel formulation (Acryloid AT 400 from Rohm & Haas) is based on hydroxyethyl methacrylate, methyl methacrylate, styrene, butyl acrylate and butyl methacrylate and a melamine curing agent.

Pieces of steel sheeting 4"×12"(9.16 cm×30.48 cm),coated with a primer based on polyester/epoxy resin, are then coated with a silver metallic base coat and finally with the clear finishing enamel. The base coat is sprayed onto the sheet to a thickness of about 0.8 mil (0.0203 mm) and air dried for 3 minutes. The clear finishing enamel coat is then sprayed onto the sheet to a thickness of about 1.5 mil (0.0381 mm). After 15 minutes air-drying, the coated sheets are baked for 30 minutes at 250° F. (121° C.).

The stabilizers under test are added to the thermoset acrylic resin finishing enamel before the enamel is sprayed onto the base coated sheet.

After storage for 3 weeks in an air-conditioned room (23° C./50% relative humidity), the coated sheets are subjected to weathering for 1300 hours according to test method ASTM G-53/77 in a QUV tester. In this test, the samples are subjected to weathering in repeated cycles for 4 hours in a humid atmosphere at 50° C. and then for 8 hours under UV light at 70° C. Subsequently, distinction of the image (DI) and the 20° gloss of the surface of the finishes are determined. High values for 20° gloss and DI are desired.

| QUV Exposure - 1300 hours<br>Stabilizer in clear coat | 20° Gloss | DI |
|---|---|---|
| Without Additive | 6 | 12 |
| 1% Compound I* | 21 | 16 |
| 1% Compound I + 2% Compound 5 | 92 | 66 |
| 1% Compound I + 2% Compound 12 | 90 | 68 |

*Compound I is 2-[2-hydroxy-3,5-di(alpha,alpha-dimethylbenzyl)-phenyl]-2H-benzotriazole.

EXAMPLE 2

In another test, the samples, prepared as in Example 1, after storage are subjected to accelerated weathering for 2230 hours in a Xenon arc (6500 Watt) Weather-Ometer.

The samples are exposed to repeated cycles for 102 minutes to the light source, then for 18 minutes to a water spray and light, at 60° C. (black panel). The results are reported below. High values for 20° gloss and DI are desired.

| Xenon arc exposure<br>Stabilizer in clear coat | 20° Gloss | DI |
|---|---|---|
| Without Additive | 44 | 6 |
| 1% Compound I | 78 | 37 |
| 1% Compound I + 2% Compound 5 | 89 | 70 |
| 1% Compound I + 2% Compound 12 | 89 | 84 |

EXAMPLE 3

Cracking Resistance

Samples described in Example 1 after being exposed in the QUV tester for 1300 hours are evaluated visually for cracking. The results are given below.

| Cracking after 1300 hours<br>Stabilizer in clear coat | Appearance of the Enamel |
|---|---|
| Without Stabilizer | Deep cracks |
| 1% Compound I | Shallow cracks |
| 1% Compound I + 2% Compound 5 | No cracking |
| 1% Compound I + 2% Compound 12 | No cracking |

EXAMPLE 4

Knoop Hardness and Enamel Appearance

Samples described in Example 1 after baking for 30 minutes at 121° C. are stored for one week at room temperature. Knoop hardness values are determined on the baked enamel and the general appearance of the enamels is noted.

| Stabilizer in clear coat | Baked Coating Knoop Hardness | Appearance of Coating Before Baking |
|---|---|---|
| Unstabilized | 11.8 | Clear |
| 1% Compound I | 11.8 | Clear |
| 1% Compound I + 2% Compound 5 | 11.6 | Clear |
| 1% Compound I + 2% Compound 12 | 10.6 | Clear |

EXAMPLE 5

Two thermoset acrylic enamels are formulated to include a benzotriazole UV-absorber and a hindered amine light stabilizer as described in Example 1.

The coated panels are exposed in the QUV tester, or in the Xenon Arc Weatherometer or in South Florida in an unheated black box at an angle of 5° to the sun. 20° gloss or distinction of image (DI) values are determined.

The thermoset acrylic enamels are based on a binder of 70% of monomers such as hydroxyethyl acrylate, styrene, acrylonitrile, butyl acrylate and acrylic acid with 30% of a melamine resin and an acid catalyst, such as p-toluenesulfonic acid, dinonylnaphthalenedisulfonic acid, dodecylbenzenesulfonic acid or phenyl acid phosphate.

Enamel A is coated over a silver metallic base coat and Enamel B is coated over a white base coat.

| | 20° Gloss Values after Hours of QUV Exposure | | | | | | Hours of QUV Exposure Till |
|---|---|---|---|---|---|---|---|
| Enamel A with | 0 | 750 | 1300 | 1600 | 2350 | 3000 | First Cracking Observed |

-continued

| | | | | | | | |
|---|---|---|---|---|---|---|---|
| No Stabilizer | 95 | 82 | 8 | 2 | — | — | 900 |
| 1% Compound I | 95 | 90 | 20 | 8 | — | — | 1100 |
| 1% Compound I plus 2% Compound 5 | 92 | 92 | 92 | 90 | 40 | 10 | 2700 |

| | 20° Gloss Values after Hours of Xenon Arc Exposure | | | | | | | | | | Hours of Xenon Exposure Till |
|---|---|---|---|---|---|---|---|---|---|---|---|
| Enamel A with | 0 | 1400 | 1850 | 2500 | 2750 | 3300 | 4050 | 5100 | 5900 | 7400 | First Cracking Observed |
| No Stabilizer | 90 | 55 | 35 | 22 | 15 | 0 | — | — | — | — | 2700 |
| 1% Compound I | 95 | 85 | 82 | 75 | 70 | 60 | 50 | 0 | — | — | 4800 |
| 1% Compound I plus 2% Compound 5 | 90 | 90 | 90 | 90 | 90 | 88 | 88 | 75 | 70 | 45 | >8500 |

| | Distinction of Image Values after Months of South Florida Exposure | | | |
|---|---|---|---|---|
| Enamel A with | 0 | 6 | 12 | 18 |
| No Stabilizer | 82 | 25 | 5 | 2 |
| 1% Compound I | 82 | 60 | 50 | 15 |
| 1% Compound I plus 2% Compound 5 | 85 | 82 | 75 | 60 |

| | Distinction of Image Values after Hours of QUV Exposure | | | | | | |
|---|---|---|---|---|---|---|---|
| Enamel B with | 0 | 200 | 1050 | 1450 | 1700 | 1840 | 2250 |
| No Stabilizer | 78 | 55 | 8 | 5 | — | — | — |
| 2% Compound I | 88 | 88 | 88 | 78 | 65 | 40 | 18 |
| 2% Compound I plus 0.5% Compound 5 | 88 | 88 | 88 | 88 | 88 | 88 | 60 |

EXAMPLE 6

In order to determine whether cure is affected at either the 121° C. normal bake temperature or at the 82° C. automotive low bake repair temperature, Enamel A (as described in Example 5) containing various stabilizer combinations is baked over a silver base coat for 30 minutes at 121° C. or for 30 minutes at 82° C.

The effectiveness of cure is assessed from Knoop hardness values, the higher numbers indicating greater hardness and hence cure.

| Enamel A containing 1% by weight Compound I plus 2% by weight of Test Compound | Knoop Hardness Values Normal Bake | Low Bake Repair |
|---|---|---|
| Unstabilized | 11.5 | 11.5 |
| Compound II* | 1-2 | — |
| Compound 5 | 11.5 | 7.0 |

*Compound II is di-(1,2,2,6,6-pentamethylpiperidin-4-yl) sebacate.

The instant compound 5 does not retard cure at the normal bake temperature and causes only a slight insignificant retardation of cure at the automotive low bake repair temperature.

EXAMPLE 7

The physical properties of Enamel A (as described in Example 5) coated over a silver metallic base coat when cured for 30 minutes at 82° C., the low bake repair temperature, are completely satisfactory as is seen in the table below.

| Enamel A containing 1% by weight Compound I plus 1.5% by weight of Test Compound | Knoop Hardness | Pendulum Hardness | Change in 20° Gloss Value after Humidity | Cross-hatch Adhesion |
|---|---|---|---|---|
| Unstabilized | 7 | 70 | 20 | 4 |
| Only Compound I | 7 | 80 | 3 | 5 |
| Compound III* | 7.5 | 80 | 7 | 4 |
| Compound 5 | 7 | 85 | 2 | 5 |

*Compound III is bis(1-acetyl-2,2,6,6-tetramethylpiperidin-4-yl) sebacate

The 20° gloss values are taken on coated panels conditioned for 96 hours in a constant humidity chamber at 38° C. and 100% relative humidity. A low change in 20° gloss value shows the coating is not adversely affected by humidity.

The cross-hatch type adhesion test involves using a multi-cut knife to prepare cross-hatches through the topcoat film and base coat on the panel. An acetate fiber adhesive tape is placed over the cross-hatch area and then is pulled off. A visual inspection of the amount of topcoat, if any, coming off with the tape as it is pulled gives a relative rating of the amount of delamination. A rating system of 5 indicating the absence of cross-hatch delamination to 0 indicating complete cross-hatch delamination is used.

It is clear that the low bake curing at 82° C. for the acid catalyzed thermoset enamels containing the N-hydroxy hindered amine light stabilizers is completely adequate.

EXAMPLE 8

The thermoset acrylic enamel of Example 5 including 0.5% of p-toluenesulfonic acid is formulated to include varying concentrations of a benzotriazole UV-absorber and a hindered amine light stabilizer of the invention. The enamel is coated over a silver metallic base coat pursuant to the procedure in Example 5 and baking is conducted for 30 minutes at 121° C. normal bake temperature.

The coated panels are exposed in the QUV exposure apparatus and the time to 50% loss of 20° gloss is determined.

| Compound | Conc. (% by wt.) | Time to 50% Loss of 20% Gloss (hours) |
|---|---|---|
| unstabilized | — | 600 |
| I | 2 | 1200 |
| I/5 | 2/1.5 | 3300 |
| I/22 | 2/1.5 | 2900 |
| I/29 | 2/1.5 | 2000 |
| I/37 | 2/1.5 | 1700 |
| unstabilized* | — | 800 |
| I* | 2 | 1500 |
| I/5* | 2/1.5 | 3400 |
| I/32* | 2/1.5 | 3400 |
| unstabilized* | — | 700 |
| IV | 3.5 | 1400 |
| IV/41 | 3.5/1.5 | 2500 |
| unstabilized* | — | 900 |
| IV/II | 3.5/0.25** | 3000 |
| IV/5 | 3.5/0.75 | 4750 |
| IV/5 | 3.5/1.5 | 5300 |
| IV/28 | 3.5/1.5 | 4500 |
| IV/29 | 3.5/1.5 | 5300 |
| IV/31 | 3.5/1.5 | 3900 |
| IV/35 | 3.5/1.5 | 4700 |
| IV/39 | 3.5/1.5 | 5100 |
| IV/40 | 3.5/1.5 | 5300 |
| unstabilized* | — | 1000 |
| IV | 3 | 2250 |
| IV/5 | 3/1 | 4700 |
| IV/27 | 3/1 | 4100 |
| IV/36 | 3/1 | 5200 |
| IV/38 | 3/1 | 4600 |
| IV/39 | 3/1 | 4200 |
| IV/40 | 3/1 | 4600 |

IV - 2-[2-hydroxy-3-tert.butyl-5-(2-omega-hydroxy-octa-(ethyleneoxy)carbonyl)-ethylphenyl]-2H-benzotriazole
*additives added to clear coat and base coat
**low concentration required due to cure retardation at higher levels

EXAMPLE 9

A polyester-melamine coil coating catalyzed with p-toluenesulfonic acid is formulated to include a benzotriazole UV absorber and a hindered amine light stabilizer of the invention. The material is applied using a wire-wound rod and an automatic drawdown apparatus onto coil primed panels to a dry thickness of 0.8 mil. The panels are baked in a 260° C. oven for 45 seconds at which time the peak metal temperature is 225° C. Two colored systems, a phthalo blue and a bronze oxide pigmented system, are tested. The panels are exposed in South Florida at an angle of 45° S. to the sun for 17 months. The color change (ΔE) of the panels are reported.

| Compound | Conc. (% by wt.) | |
|---|---|---|
| | | ΔE of Brown Panels |
| — | — | 6.7 |
| IV/41 | 3/3 | 5.5 |
| | | ΔE of Blue Panels |
| — | — | 7.0 |
| IV/40 | 3/3 | 5.2 |

EXAMPLE 10

The thermoset acrylic enamel of Example 5 including an acid catalyst such as p-toluenesulfonic acid, dinonylnaphthalenedisulfonic acid or dodecylbenzenesulfonic acid is formulated to include a hindered amine light stabilizer of the invention. Coil coated aluminum panels primed with an epoxy primer are coated with 0.6-0.8 mil of a silver metallic basecoat and finally with 1.6-1.8 mil of the clear finishing enamel. After 5-10 minutes of air drying, the coated panels are baked for 30 minutes at 130° C.

The coated panels are exposed in the QUV exposure apparatus and the 20° gloss of the samples are determined at various intervals.

| Compound | Conc. (% by wt.) | 20° Gloss (at hours) 0 | 800 | 1600 | 2000 | 2400 | 2800 | 3200 |
|---|---|---|---|---|---|---|---|---|
| — | — | 92 | 69 | 45* | | | | |
| 5 | 1 | 91 | 84 | 68 | 67 | 54 | 56 | 37 |
| 40 | 1 | 91 | 87 | 65 | 42 | 41 | 25* | |

*cracking

What is claimed is:

1. A stabilized stoving lacquer composition comprising
(a) an acid catalyzed thermoset resin based on hot crosslinkable acrylic, polyester, polyurethane, polyamide or alkyd resins, and
(b) an effective oxidative and light stabilizing amount of an N-hydroxyl substituted hindered amine derivative corresponding to the formulae A to O

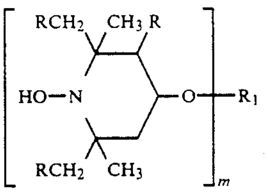
(A)

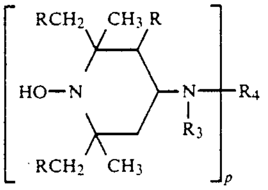
(B)

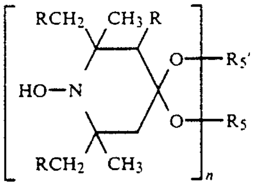
(C)

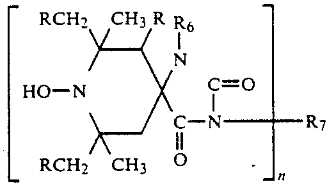
(D)

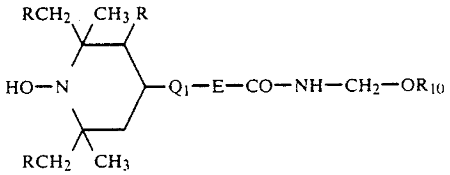
(E)

-continued (F)

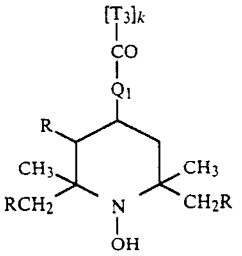

(G)

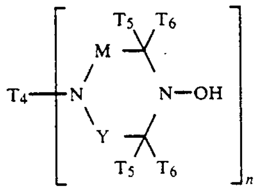

(H)

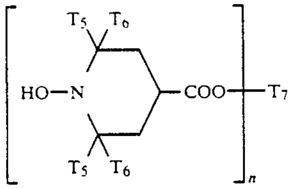

(I)

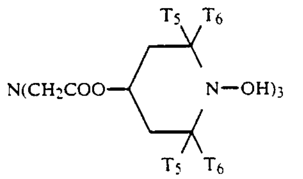

(J)

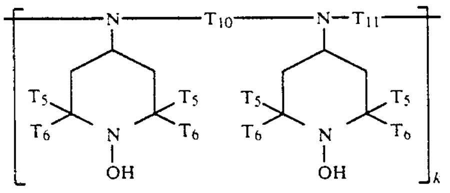

(K)

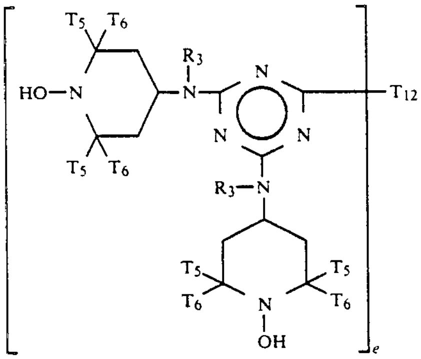

(L)

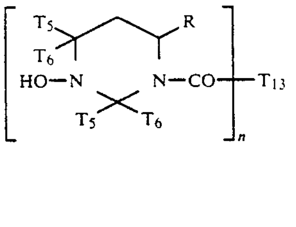

-continued (M)

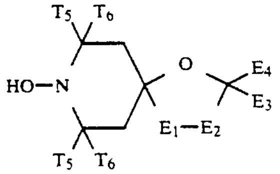

(N)

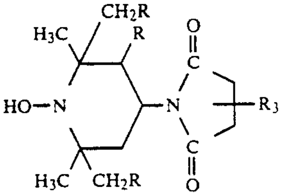

(O)

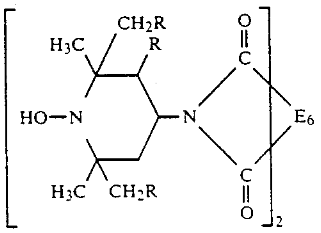

wherein

R is hydrogen or methyl, m is 1–4, when m is 1, $R_1$ is hydrogen, $C_1$-$C_{18}$ alkyl optionally interrupted by one or more oxygen atoms, $C_2$-$C_{12}$ alkenyl, $C_6$-$C_{10}$ aryl, $C_7$-$C_{12}$-aralkyl, glycidyl, a monovalent acyl radical or an aliphatic, cycloaliphatic, araliphatic or aromatic carboxylic acid, or of carbamic acid; or

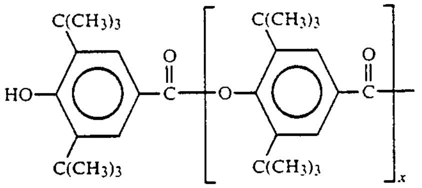

wherein x is 0 or 1, or

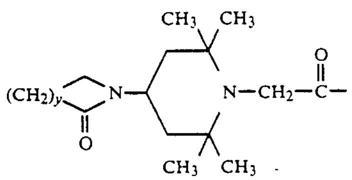

wherein y is 2–4;

when m is 2, $R_1$ is $C_1$-$C_{12}$ alkylene, $C_4$-$C_{12}$ alkenylene, xylylene, a divalent acyl radical of an aliphatic, cycloaliphatic, araliphatic or aromatic dicarboxylic acid or of a dicarbamic acid;

when m is 3, $R_1$ is a trivalent acyl radical of an aliphatic, unsaturated aliphatic, cycloaliphatic, or aromatic tricarboxylic acid;

when m is 4, $R_1$ is a tetravalent acyl radical of a saturated or unsaturated aliphatic or aromatic tetracarboxylic acid;

p is 1, 2 and 3, $R_3$ is hydrogen, $C_1$-$C_{12}$ alkyl, $C_5$-$C_7$ cycloalkyl, $C_7$-$C_9$ aralkyl, $C_2$-$C_{18}$ alkanoyl, $C_3$-$C_5$ alkenoyl or benzoyl;

when p is 1, $R_4$ is hydrogen, $C_1$-$C_{18}$ alkyl, $C_5$-$C_7$ cycloalkyl, $C_2$-$C_8$ alkenyl unsubstituted or substituted by a cyano, carbonyl or carbamide group, aryl, aralkyl, or it is glycidyl, a group of the formula $—CH_2—CH(OH)—Z$ or of the formula $—CO—Z$ or $—CONH—Z$ wherein Z is hydrogen, methyl or phenyl, or a group of the formulae

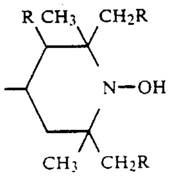

or

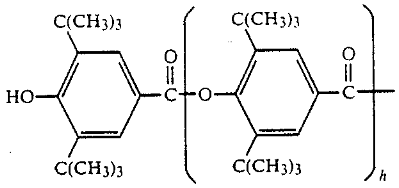

with h as 0 or 1;

or $R_3$ and $R_4$ together when p is 1 can be alkylene of 4 to 6 carbon atoms or 2-oxo-polyalkylene or the cyclic acyl radical of an aliphatic or aromatic 1,2- or 1,3-dicarboxylic acid, when p is 2, $R_4$ is a direct bond or is $C_2$-$C_{12}$ alkylene, $C_6$-$C_{12}$ arylene, xylylene, a $—CH_2CH(OH)—CH_2$ group, or a group $—CH_2—CH(OH)—CH_2—O—X—O—CH_2—CH(OH)—CH_2—$ wherein X is $C_2$-$C_{10}$ alkylene, $C_6$-$C_{15}$ arylene or $C_6$-$C_{12}$ cycloalkylene; or, provided that $R_3$ is not alkanoyl, alkenoyl or benzoyl, $R_4$ can also be divalent acyl radical of an aliphatic, cycloaliphatic or aromatic dicarboxylic acid or dicarbamic acid, or can be the group —CO—; or

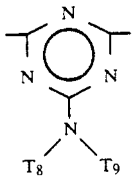

where $T_8$ and $T_9$ are independently hydrogen, alkyl of 1 to 18 carbon atoms, or $T_8$ and $T_9$ together are alkylene of 4 to 6 carbon atoms or 3-oxapentamethylene;

when p is 3, $R_4$ is 2,4,6-triazinyl, n is 1 or 2, when n is 1, $R_5$ and $R'_5$ are independently $C_1$-$C_{12}$ alkyl, $C_2$-$C_{12}$ alkenyl, $C_7$-$C_{12}$ aralkyl, or $R_5$ is also hydrogen, or $R_5$ and $R'_5$ together are $C_2$-$C_8$ alkylene or hydroxyalkylene or $C_4$-$C_{22}$ acyloxyalkylene;

when n is 2, $R_5$ and $R'_5$ together are $(—CH_2)_2C(CH_2—)_2$;

$R_6$ is hydrogen, $C_1$-$C_{12}$ alkyl, allyl, benzyl, glycidyl or $C_2$-$C_6$ alkoxyalkyl;

when n is 1, $R_7$ is hydrogen, $C_1$-$C_{12}$ alkyl, $C_3$-$C_5$ alkenyl, $C_7$-$C_9$ aralkyl, $C_5$-$C_7$ cycloalkyl, $C_2$-$C_4$ hydroxyalkyl, $C_2$-$C_6$ alkoxyalkyl, $C_6$-$C_{10}$ aryl, glycidyl, a group of the formula $—(CH_2)_t—COO—Q$ or of the formula $—(CH_2)_t—O—CO—Q$ wherein t is 1 or 2, and Q is $C_1$-$C_4$ alkyl or phenyl; or when n is 2, $R_7$ is $C_2$-$C_{12}$ alkylene, $C_6$-$C_{12}$ arylene, a group $—CH_2CH(OH)—CH_2—O—X—O—CH_2—CH(OH)—CH_2—$ wherein X is $C_2$-$C_{10}$ alkylene, $C_6$-$C_{15}$ arylene or $C_6$-$C_{12}$ cycloalkylene, or a group $—CH_2CH(OZ')CH_2—(OCH_2—CH(OZ')CH_2)_2—$ wherein Z' is hydrogen, $C_1$-$C_{18}$ alkyl, allyl, benzyl, $C_2$-$C_{12}$ alkanoyl or benzoyl;

$Q_1$ is $—N(R_8)—$ or —O—;

E is $C_1$-$C_3$ alkylene, the group $—CH_2—CH(R_9)—O—$ wherein $R_9$ is hydrogen, methyl or phenyl, the group $—(CH_2)_3—NH—$ or a direct bond;

$R_{10}$ is hydrogen or $C_1$-$C_{18}$ alkyl;

$R_8$ is hydrogen, $C_1$-$C_{18}$ alkyl, $C_5$-$C_7$ cycloalkyl, $C_7$-$C_{12}$ aralkyl, cyanoethyl, $C_6$-$C_{10}$ aryl, the group $—CH_2—CH(R_9)—OH$ wherein $R_9$ has the meaning defined above; a group of the formula

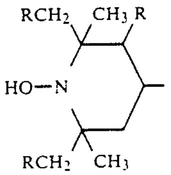

or a group of the formula

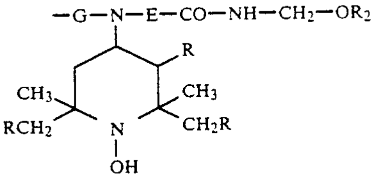

wherein G can be $C_2$-$C_6$ alkylene or $C_6$-$C_{12}$ arylene; or $R_8$ is a group $—E—CO—NH—CH_2—OR_{10}$;

$T_3$ is ethylene or 1,2-propylene, or is the repeating structural unit derived from an alpha-olefin copolymer with an alkyl acrylate or methacrylaate;

k is 2 to 100;

$T_5$ is methyl, $T_6$ is methyl or ethyl, or $T_5$ and $T_6$ together are tetramethylene or pentamethylene;

M and Y are independently methylene or carbonyl;

$T_7$ is the same as $R_7$;

$T_{10}$ and $T_{11}$ are independently alkylene of 2 to 12 carbon atoms, or $T_{11}$ is

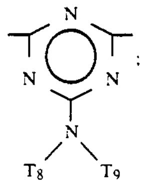
;

$T_{12}$ is piperazinyl, $$-NR_{11}-(CH_2)_f-NR_{11}-$$

or $$-NH(CH_2)_a-N(CH_2)_b-N[(CH_2)_c-N]_dH$$

where $R_{11}$ is the same as $R_3$ or is also

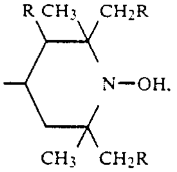

a, b and c are independently 2 or 3, d is 0 or 1 and f is 0–20;

e is 2, 3 or 4;

$T_{13}$ is the same as R with the proviso that $T_{13}$ cannot be hydrogen when n is 1;

$E_1$ and $E_2$, being different, each are —CO— or —N($E_5$)— where $E_5$ is hydrogen, $C_1$-$C_{12}$ alkyl or alkoxycarbonylalkyl of 4 to 22 carbon atoms;

$E_3$ is hydrogen, alkyl of 1 to 30 carbon atoms, phenyl, naphthyl, said phenyl or said naphthyl substituted by chlorine or by alkyl of 1 to 4 carbon atoms, or phenylalkyl or 7 to 12 carbon atoms, or said phenylalkyl substituted by alkyl of 1 to 4 carbon atoms;

$E_4$ is hydrogen, alkyl of 1 to 30 carbon atoms, phenyl, naphthyl or phenylalkyl of 7 to 12 carbon atoms, or $E_3$ and $E_4$ together are polymethylene of 4 to 17 carbon atoms, or said polymethylene substituted by up to four alkyl groups of 1 to 4 carbon atoms, and $E_6$ is an aliphatic or aromatic tetravalent radical.

2. The composition according to claim 1 wherein the compound of component (b) is selected from the group consisting of 1-hydroxy-4-salicyloxy-2,2,6,6-tetramethylpiperidine;

1-hydroxy-2,2,6,6-tetramethylpiperidin-4-yl 3,5-ditert-butyl-4-hydroxyhydrocinnamate;

di(1-hydroxy-2,2,6,6-tetramethylpiperidin-4-yl) sebacate;

di-(1-hydroxy-2,3,6-trimethyl-2,6-diethyl-piperidin-4-yl) phthalate;

di-(1-hydroxy-2,2,6,6-tetramethylpiperidin-4-yl) n-butyl-(3,5-di-tert-butyl-4-hydroxybenzyl)malonate;

hexane-1',6'-bis-(4-carbamoyloxy-1-hydroxy-2,2,6,6-tetramethylpiperidine);

N,N'-bis-(1-hydroxy-2,2,6,6-tetramethylpiperidin-4-yl)hexamethylene-1,6-diacetamide;

4-(N-cyclohexylacetamido)-1-hydroxy-2,2,6,6-tetramethylpiperidine;

N-(1-hydroxy-2,2,6,6-tetramethylpiperidin-4-yl)-epsilon-caprolactam;

N-(1-hydroxy-2,2,6,6-tetramethylpiperidin-4-yl)-succinimide;

N-(1-hydroxy-2,3,6-trimethyl-2,6-diethyl-piperidin-4-yl)-maleimide;

8-aza-2,7,7,9,9-pentamethyl-8-hydroxy-1,4-dioxyspiro[4.5]decane;

9-aza-3-hydroxymethyl-3-ethyl-9-hydroxy-8,8,10,10-tetramethyl-1,5-dioxaspiro[5.5]undecane;

3-n-octyl-1,3,8-triaza-8-hydroxy-7,7,9,9-tetramethyl-spiro[4.5]decan-2,4-dione;

8-hydroxy-2,7,7,9,9-pentamethyl-2-hexyl-1-oxa-3,8-diazaspiro[4.5]decan-4-one;

3-hydroxy-2,2,4,4-tetramethyl-7-oxa-3,20-diazadispiro[5.1.11.2]heneicosan-21-one;

1,1'-ethylenebis-(4-hydroxy-3,3,5,5-tetramethylpiperazin-2-one);

1,1'-sebacoyl-bis(3-hydroxy-2,2,4,4,6-pentamethylhexahydropyrimidine); hydroxylamine derivative of polycondensation product of 2,4-dichloro-6-tert-octylamino-s-triazine and 4,4'-hexamethylenebis-(amino-2,2,6,6-tetramethylpiperidine);

N,N',N'',N'''-tetrakis[4,6-bis(butyl-(1-hydroxy-2,2,6,6-tetramethylpiperidin-4-yl)amino)-s-triazin-2-yl]-1,10-diamino-4,7-diazadecane;

hydroxylamine derivative of polycondensation product of 2,4-dichloro-6-morpholino-s-triazine and 4,4'-hexamethylenebis-(amino-2,2,6,6-tetramethyl-piperidine);

15-n-octadecyl-7-hydroxy-7,15-diazadispiro[5.1.5.3]-hexadecane-14,16-dione;

4-benzoyloxy-1-hydroxy-2,2,6,6-tetramethylpiperidine;

3-hydroxy-2,2,4,4-tetramethyl-20-(2-lauryloxycarbonyl)ethyl-7-oxa-3,20-diazadispiro[5.1.11.2]heneicosan-21-one;

di-(1-hydroxy-2,2,6,6-tetramethylpiperidin-4-yl) phthalate;

1-hydroxy-2,2,6,6-tetramethylpiperidin-4-yl stearate;

4-(4-tert.butylbenzoyloxy)-1-hydroxy-2,2,6,6-tetramethylpiperidine;

(1-hydroxy-2,2,6,6-tetramethylpiperidin-4-yl)-4-hydroxy-3,5-di-tert.butylbenzoate;

(1-hydroxy-2,2,6,6-tetramethylpiperidin-4-yl)-4-(4-hydroxy-3,5-di-tert.butylbenzoate)-3,5-di-tert.butylbenzoate;

(1-hydroxy-2,2,6,6-tetramethylpiperidin-4-yl)-[4-(2-oxazepin-1-yl)-2,2,6,6-tetramethylpiperidin-4-yl) acetate;

alpha,alpha'-di-(1-hydroxy-2,2,6,6-tetramethylpiperidin-4-oxy)-p-xylene;

di-(1-hydroxy-2,2,6,6-tetramethylpiperidin-4-yl) diethylmalonate;

N-n-butyl-N-(1-hydroxy-2,2,6,6-tetramethylpiperidin-4-yl)-4-hydroxy-3,5-di-tert.butylbenzamide;

tetrakis (1-hydroxy-2,2,6,6-tetramethyl-4-piperidyl)-1,2,3,4-butane-tetracarboxylate;

di-(1-hydroxy-2,2,6,6-tetramethylpiperidin-4-yl)isophthalate;

di-(1-hydroxy-2,2,6,6-tetramethylpiperidin-4-yl)n-butylmalonate; and di-(1-hydroxy-2,2,6,6-tetramethylpiperidin-4-yl)-2-(4-hydroxy 3,5-di-t.-butylbenzyl)-n-butylmalonate.

3. The composition according to claim 2 wherein component (b) is di-(1-hydroxy-2,2,6,6-tetramethylpiperidin-4-yl) sebacate.

4. The composition according to claim 2 wherein component (b) is N-(1-hydroxy-2,2,6,6-piperidin-4-yl)epsilon-caprolactam.

5. The composition according to claim 2, wherein component (b) is di-(1-hydroxy-2,2,6,6-tetramethyl-piperidin-4-yl)phthalate.

6. The composition according to claim 2, wherein component (b) is di-(1-hydroxy-2,2,6,6-tetramethyl-piperidin-4-yl)isophthalate.

7. The composition according to claim 2, wherein component (b) is di-(1-hydroxy-2,2,6,6-tetramethyl-piperidin-4-yl)n-butylmalonate.

8. The composition according to claim 2, where component (b) is di-(1-hydroxy-2,2,6,6-tetramethylpiperin-4-yl)-2-(4-hydroxy 3,5-di-t.butylbenzyl)-n-butylmalonate.

9. The composition according to claim 1, wherein the N-hydroxyl substituted compound of component (b) is present in an amount of 0.1 to 5% by weight, based on the resin solids.

10. The composition according to claim 20 which additionally contains a UV absorber selected from the group consisting of benzophenones, benzotriazoles, aryl-s-triazines, acrylic acid derivatives, organic nickel compounds and oxanilides.

11. A composition according to claim 10 which contains abenzotriazole UV absorber selected from the group consisting of 2-[2-hydroxy-3,5-di(alpha,alpha-dimethylbenzyl)phenyl]-2H-benzotriazole, 2-(2-hydroxy-3,5-di-tertoctylphenyl)-2H-benzotriazole, 2-(2-hydroxy-3-alpha,alpha-dimethylbenzyl-5-tert-octylphenyl)-2H-benzotriazole, 2-(2-hydroxy-3-tert-octyl-5-alpha,alpha-dimethylbenzylphenyl)-2H-benzotriazole, 2-(2-hydroxy-5-tert-octylphenyl)-2H-benzotriazole, 2-[2-hydroxy-3-tert-butyl-5-(2-(omega-hydroxy-octa(ethyleneoxy)carbonyl)-ethylphenyl]-2H-benzotriazole, 2-(2-hydroxy-3,5-di-tert-amylphenyl)-2H-benzotriazole, dodecylated 2-(2-hydroxy-5-methylphenyl)-2H-benzotriazole, 5-chloro-2-[2-hydroxy-3,5-di(alpha,alpha-dimethylbenzyl)-phenyl]-2H-benzotriazole, 5-chloro-2-(2-hydroxy-3,5-di-tert-octylphenyl)-2H-benzotriazole, 5-chloro-2-(2-hydroxy-3-alpha,alpha-dimethyl-benzyl-5-tert-octylphenyl)-2H-benzotriazole, 5-chloro-2-(2-hydroxy- 3-tert-octyl-5-alpha,alpha-dimethylbenzyl-phenyl)-2H-benzotriazole, 5-chloro-2-[2-hydroxy-3-tert-butyl-5-(2-(omega-hydroxyocta(ethyleneoxy)-ethylphenyl]-2H-benzotriazole, 5-chloro-2-(2-hydroxy-5-tert-octyl-phenyl)-2H-benzotriazole, 5-chloro-2-(2-hydroxy-3,5-di-tert-amylphenyl)-2H-benzotriazole and 5-chloro-2-[2-hydroxy-3-tert.-butyl-5-(2-octyloxycarbonyl)ethylphenyl]-2H-benzotriazole.

12. The composition according to claim 11 wherein the benzotriazole is 2-[2-hydroxy-3,5-di(alpha,alpha-dimethylbenzyl)-phenyl]-2H-benzotriazole, 2-[2-hydroxy-3-tert.-butyl-5-(2-(omega-hydroxy-octa(ethyleneoxy)carbonyl)ethylphenyl]-2H-benzotriazole, 2-[2-hydroxy-3-tert.butyl-5-(2-octyloxycarbonyl)ethylphenyl]-2H-benzotriazole or 5-chloro-2-[2-hydroxy-3-tert.butyl-5-(2-octyloxycarbonyl)ethylphenyl]-2H-benzotriazole.

13. The composition according to claim 10 wherein the total amount of component (b) plus UV absorber is 0.2 to 20% by weight based on the solids.

14. The composition according to claim 10 which additionally contains a phosphite or phosphonite antioxidant.

15. The composition according to claim 14 which additionally contains a hindered phenol antioxidant.

16. The composition according to claim 1 which is an enamel of high solids content for industrial finishes.

17. The composition according to claim 1 which is a finishing enamel for automobiles.

18. The composition according to claim 1 which is a coil coating.

* * * * *